United States Patent [19]

Eichler et al.

[11] Patent Number: 4,783,541

[45] Date of Patent: Nov. 8, 1988

[54] PROCESS FOR ISOMERIZING ALKYLTHIOPHENES

[75] Inventors: Klaus Eichler, Eschborn; Ernst I. Leupold, Neu-Anspach, both of Fed. Rep. of Germany

[73] Assignee: Hoechst Aktiengesellschaft, Frankfurt am Main, Fed. Rep. of Germany

[21] Appl. No.: 135,504

[22] Filed: Dec. 18, 1987

Related U.S. Application Data

[63] Continuation of Ser. No. 040,759, Apr. 16, 1987, abandoned, which is a continuation of Ser. No. 919,548, Oct. 15, 1986, abandoned, which is a continuation of Ser. No. 774,936, Sep. 11, 1985, abandoned.

[30] Foreign Application Priority Data

Sep. 13, 1984 [DE] Fed. Rep. of Germany ....... 3433813

[51] Int. Cl.$^4$ .......................................... C07D 333/08
[52] U.S. Cl. ........................................ 549/83; 549/86
[58] Field of Search ................................. 349/83, 86

[56] References Cited

U.S. PATENT DOCUMENTS 3,251,847  5/1966  Landis et al. ..................... 549/86

FOREIGN PATENT DOCUMENTS 2757816  12/1977  Fed. Rep. of Germany .
 860673   2/1961  United Kingdom .
1334243  10/1973  United Kingdom .
1345203   1/1974  United Kingdom .

OTHER PUBLICATIONS

Ullman's Encyclopedia of Industrial Chemistry, 4th Edition, vol. 23, p. 216.
Atlas of Zeolite Structure Types, pp. 10, 11 and 12.
"Rentasil Family of High Silicon Crystalline Materials" in Special Publication No. 33 of the Chemical Society, London 1980.

Primary Examiner—Alan Siegel
Attorney, Agent, or Firm—Curtis, Morris & Safford

[57] ABSTRACT

The invention relates to a process for isomerizing alkylthiophenes on zeolite catalysts. In particular, methylthiophene and ethylthiophene can be isomerized by this process. Suitable zeolites are in particular synthetic zeolites of the pentasil, mordenite of faujasite type in their acid form.

5 Claims, No Drawings

PROCESS FOR ISOMERIZING ALKYLTHIOPHENES

This is a continuation of Ser. No. 040,759, filed 4/16/87, now abandoned, which is a continuation of Ser. No. 919,548, filed 10/15/86, now abandoned, which is a continuation of Ser. No. 774,936, filed 9/11/85, now abandoned.

The present invention relates to a process for isomerizing alkylthiophenes.

Alkylated thiophenes are valuable intermediates. Thus, for example, the methylthiophenes are used as starting materials for the preparation of thenyl chloride and thiophenecarboxylic acid, which are required in the preparation of pharmaceuticals (Ullmanns Enzyklopä die der technischen Chemie [Ullmann's Encyclopedia of Industrial Chemistry], 4th Edition, Volume 23, page 219). They are generally prepared by cyclization reactions of olefins or alcohols with $H_2S$ or $CS_2$ (British Pat. No. 1,345,203, and German Offenlegungsschrift No. 2,757,816). The synthesis of 3-substituted alkylthiophenes here requires branched starting materials, some of which are very expensive or are not available. Simple and inexpensive methods for the preparation of 3-alkylthiophenes on an industrial scale have not hitherto been described.

It has now been found that alkylated thiophenes can be isomerized on zeolite catalysts in high yield.

The invention therefore relates to a process for isomerizing alkylthiophenes, which comprises contacting an alkylthiophene or a mixture of alkylthiophenes with a zeolite catalyst. In particular, the invention relates to a process for isomerizing methylthiophene or ethylthiophene on a zeolite catalyst. The term "alkylthiophenes" is intended to comprise all thiophenes which contain one to three straight-chain or branched alkyl groups having one to six carbon atoms, i.e. for example methyl-, ethyl-, isopropyl-, dimethyl-, diethyl- or di-t-butyl-thiophene.

In the light of the state of the art, it was surprising and in no way foreseeable that alkylthiophenes can be isomerized in such a simple way with yields as high as those shown in the Examples, and that 3-alkylthiophenes, which hitherto have been difficult to prepare, can readily be prepared in this way from industrially available 2-alkylthiophenes.

Example 1 shows that 2-methylthiophene can be isomerized to 3-methylthiophene in good yield on H-ZSM-5. Hardly any by-products appear in this case. The isomerization proceeds even more advantageously at higher temperature (Example 2). As shown by the isomerization of 3-methylthiophene to 2-methylthiophene (Example 3), the thermodynamic equilibrium is reached independently to the starting material. Example 4 shows that 2-ethylthiophene can be isomerized to 3-ethylthiophene even at 300° C. in high yield.

To carry out the process according to the invention, an alkylthiophene or a mixture of two or more alkylthiophenes is contacted with the zeolite catalyst.

Suitable zeolites are in general both natural and synthetic zeolites, preferably synthetic zeolites of the pentasil, mordenite or faujasite types, in particular synthetic zeolites of the pentasil type.

The definition by Kokotailo and Meier ("Pentasil family of high silicon crystalline materials" in Special Publication Np. 33 of the Chemical Society, London, 1980) here applies to the term pentasils. The pentasil family comprises, for example, the synthetic zeolites ZSM-5 (U.S. Pat. No. 3,702,886), ZMS-8 (British Pat. No. 1,334,243), ZMS-11 (U.S. Pat. No. 3,709,979) and ZMS-23 (U.S. Pat. No. 4,076,842).

The Si/Al ratio of the pentasils is preferably 20 to 2,000, and that of the mordenites is preferably 5 to 100. Pentasils or mordenites of a higher aluminum content can here be adjusted to the desired Si/Al ratio by removing a part of the aluminum from the zeolite lattice by means of a treatment with mineral acids, organic acids or chelating substances.

In the process according to the invention, the zeolites are preferably used in their acid form. These acid forms can be prepared by known methods from the alkali metal forms, such as are as a rule obtained in the zeolite synthesis or occur as natural products, by complete or partial ion exchange. For example, a conventional method for preparing the H form of a zeolite comprises converting the alkali metal form initially by partial or complete ion exchange with an ammonium salt solution into the ammonium form and then converting the latter into the H form by calcination. However, the forms exchanged with alkali metal ions, alkaline earth metal ions and rare earth metal ions also show a catalytic activity.

Those zeolites are also suitable for the process according to the invention in which aluminum or silicon atoms are replaced by other lattice atoms, such as boron, iron, gallium, germanium, titanium or zirconium.

The zeolite catalysts according to the invention are in general composed of the catalytically active zeolite component and a binder material. The latter is necessary in order to bring the zeolite into an external form which is suitable for the process according to the invention.

Suitable binder materials are above all the oxides or hydroxides of aluminum and the oxides or hydroxides of silicon, as well as layer silicates, for example those of the kaolin or montmorillonite family.

Before the zeolite catalyst thus prepared is used in the isomerization reaction according to the invention, it is usually first activated by calcination at temperatures between 300° and 700° C. To obtain better stabilization of the catalyst, it is sometimes advantageous to carry out the calcination in the presence of steam, ammonia or mixtures thereof.

If the process is to be carried out in the gas phase, an advantageous simple procedure for effecting the isomerization according to the invention comprises passing the alkylthiophene or the alkylthiophenes first from a metering device into a vaporization zone and then passing the resulting gas through an externally heated reaction tube filled with the catalyst. When the isomerization is carried out in the liquid phase, the thiophene or thiophenes, diluted if necessary, are first heated and then passed in the liquid form through the reaction tube filled with the catalyst.

Mixing with hydrogen, nitrogen and/or another carrier gas, hydrogen being preferred, is also carried out, if desired, in the vaporization or heating zone. It has here proved to be advantageous to heat these gases to the reaction temperature before the mixing.

The loading of the zeolite catalyst—expressed as LHSV (liquid hourly space velocity, $h^{-1}$)—is here in general between 0.05 and 10 $h^{-1}$, preferably between 0.1 and 5 $h^{-1}$.

The isomerization according to the invention is in general carried out at temperatures between 150° and 550° C., preferably at 200° to 450° C., and under pressures of 0.1 to 10 bar, preferably under normal pressure.

After leaving the reactor, the reaction products are cooled in order to separate off the condensable fractions. The isomerization according to the invention is, however, not restricted to this procedure (fixed-bed reactor), but can in principle also be carried out in other suitable reactor types (for example in a fluidized-bed reactor).

The resulting isomer mixture can be separated by distillation in accordance with known processes. The unconverted starting product can be recycled into the reactor.

If the activity of the catalyst decreases slowly due to carbonization, it can be regenerated from time to time. This is effected by passing oxygen, air, nitrogen/air, oxygen/air, oxygen/inert gas or air/inert gas over the deactivated catalyst at temperatures between 300° and 650° C. Nitrogen/air is here preferred. During the regeneration, the temperature should not exceed 650° C. at any point of the reactor.

The invention will be explained by the Examples which follow, but these are not intended to represent any restriction.

EXAMPLES

Preparation of the catalyst 100 g of ZSM-5 powder in the Na form (U.S. Pat. No. 3,702,886, Example 1) were treated three times for 5 hours with 1-molar ammonium chloride solution at 100° C., washed, dried and calcined in air for 5 hours at 550° C. 65 g of the resulting powder were processed with 35 g of $Al_2O_3$ to give extrudates of 1.6 mm diameter, the latter were calcined at 500° C. for 4 hours, comminuted to a particle size of 0.25 to 1.0 mm and calcined at 450° C. for 2 hours in a nitrogen stream.

Description of the apparatus

A tube reactor of glass, of 16 mm internal diameter and 50 cm length, was charged with 15 ml of the catalyst described above, and glass beads were placed on top (for vaporizing the liquid reactants). The reactor was located in an electrically heated oven. Liquid reactants were fed via a metering pump, and gases were fed in from a gas supply comprising reducing valves and instruments for measuring the pressure and the flow rate. The condensable reaction products were condensed in a cold trap at 0° C. and analyzed by gas chromatography.

EXAMPLE 1

Isomerization of 2-methylthiophene 6 ml/h of 2-methylthiophene were passed together with 4.5 liters/h of hydrogen over the catalyst described above. After a brief initial period of about 15 minutes for setting constant reaction conditions, the receiver was changed every hour and the contents were then analyzed. Table 1 shows the results.

TABLE 1

| | | Isomerization of 2-methylthiophene | | | |
|---|---|---|---|---|---|
| | | | Product composition | | |
| Duration (h) | Temperature (°C.) | Thiophene (% by weight) | 2-Methylthiophene (% by weight) | 3-Methylthiophene (% by weight) | Dimethylthiophenes (% by weight) |
| 1 | 200 | 0,1 | 98.5 | 0.2 | 0.1 |
| 2 | 200 | 0,1 | 99.1 | 0.1 | 0.2 |
| 3 | 230 | 0,1 | 98.4 | 0.7 | 0.2 |
| 4 | 260 | 0,5 | 89.7 | 8.0 | 0.6 |
| 5 | 260 | 0,2 | 89.4 | 9.6 | 0.3 |
| 6 | 300 | 0,7 | 70.0 | 26.9 | 1.4 |
| 7 | 300 | 0,5 | 77.5 | 20.4 | 1.0 |
| 8 | 330 | 0,9 | 53.3 | 42.3 | 1.6 |
| 9 | 330 | 0,6 | 58.2 | 39.5 | 1.4 |
| 10 | 330 | 0,5 | 62.2 | 36.0 | 1.0 |
| 15 | 330 | 0,3 | 71.2 | 26.2 | 1.7 |
| 20 | 330 | 0,3 | 76.8 | 22.2 | 0.4 |
| 25 | 330 | 0,2 | 84.6 | 14.8 | 0.3 |
| 30 | 330 | 0,2 | 89.2 | 10.0 | 0.3 |

EXAMPLE 2

(Isomerization of 2-methylthiophene)

6 ml/h of 2-methylthiophene were passed together with 4.5 liters/h of hydrogen over the catalyst described above. After a brief initial period of 15 minutes for setting constant reaction conditions, the receiver was changed every hour and the contents were analysed. Table 2 shows the results.

TABLE 2

| | | Isomerization of 2-methylthiophene | | | |
|---|---|---|---|---|---|
| | | | Product composition | | |
| Duration (h) | Temperature (°C.) | Thiophene (% by weight) | 2-Methylthiophene (% by weight) | 3-Methylthiophene (% by weight) | Dimethylthiophenes (% by weight) |
| 1 | 300 | 1.5 | 53.9 | 40.0 | 3.6 |
| 2 | 300 | 0.6 | 68.6 | 29.3 | 1.1 |
| 3 | 300 | 0.5 | 78.9 | 19.3 | 1.0 |
| 4 | 300 | 0.4 | 80.9 | 17.6 | 0.8 |
| 5 | 330 | 0.8 | 57.6 | 39.6 | 1.7 |
| 8 | 330 | 0.4 | 69.3 | 29.7 | 0.6 |
| 9 | 360 | 0.7 | 51.6 | 46.0 | 1.3 |
| 12 | 360 | 0.6 | 52.8 | 44.6 | 0.8 |
| 13 | 390 | 1.2 | 46.9 | 49.3 | 1.9 |
| 16 | 390 | 0.8 | 48.7 | 48.5 | 1.4 |

TABLE 2-continued

Isomerization of 2-methylthiophene

| Duration (h) | Temperature (°C.) | Thiophene (% by weight) | 2-Methyl-thiophene (% by weight) | 3-Methyl-thiophene (% by weight) | Dimethyl-thiophenes (% by weight) |
|---|---|---|---|---|---|
| 17 | 420 | 2.0 | 46.7 | 47.3 | 2.7 |
| 20 | 420 | 1.1 | 47.7 | 48.0 | 1.1 |
| 23 | 420 | 0.8 | 48.6 | 48.9 | 1.1 |
| 25 | 450 | 2.0 | 44.7 | 47.3 | 2.3 |
| 29 | 450 | 1.0 | 45.2 | 48.9 | 1.4 |
| 33 | 450 | 0.8 | 48.0 | 52.1 | 1.1 |
| 39 | 450 | 0.7 | 45.8 | 51.8 | 0.9 |

EXAMPLE 3

(Isomerization of 3-methylthiophene)

The test described in Example 2 was continued, but using 3-methylthiophene instead of 2-methylthiophene from the 39th hour. Table 3 shows the results.

TABLE 3

Isomerization of 3-methylthiophene

| Duration (h) | Temperature (°C.) | Thiophene (% by weight) | 2-Methyl-thiophene (% by weight) | 3-Methyl-thiophene (% by weight) | Dimethyl-thiophene (% by weight) |
|---|---|---|---|---|---|
| 40 | 450 | 0.5 | 43.2 | 54.4 | 0.8 |
| 41 | 450 | 0.5 | 49.2 | 49.1 | 0.8 |
| 42 | 450 | 0.5 | 46.1 | 52.3 | 0.7 |
| 43 | 450 | 0.5 | 48.2 | 49.7 | 1.0 |

EXAMPLE 4

(Isomerization of 2-ethylthiophene)

6 ml/h of 2-ethylthiophene and 4.5 liters/h of hydrogen were passed over the catalyst described in Example 1. After a brief initial period of about 15 minutes for setting constant reaction conditions, the receiver was changed every hour and the contents were then analyzed. Table 4 shows the results.

TABLE 4

Isomerization of 2-ethylthiophene

| Duration (h) | Temperature (°C.) | Thiophene (% by weight) | 2-Ethyl-thiophene (% by weight) | 3-Ethyl-thiophene (% by weight) | Diethyl-thiophene (% by weight) |
|---|---|---|---|---|---|
| 1 | 300 | 2.0 | 46.3 | 40.3 | 4.2 |
| 3 | 300 | 0.7 | 51.4 | 45.2 | 1.0 |
| 5 | 300 | 0.6 | 53.2 | 44.2 | 0.7 |
| 7 | 300 | 0.4 | 57.6 | 40.3 | 0.9 |

We claim:

1. A process for isomerizing alkylthiophenes, which process is carried out in the gaseous phase at temperatures from about 300°–450° C., which comprises contacting an alkylthiophene or a mixture of alkylthiophenes with an acid zeolyte catalyst of the pentasil type.

2. The process as claimed in claim 1, wherein the alkylthiophene is a methylthiophene.

3. The process as claimed in claim 1, wherein the alkylthiophene is an ethyl thiophene.

4. The process as claimed in claim 1, wherein the catalyst is H-ZSM-5.

5. The process as claimed in claim 1, wherein the alkylthiophene is 2-methylthiophene.

* * * * *